United States Patent [19]

Ouchi

[11] Patent Number: 5,820,546
[45] Date of Patent: Oct. 13, 1998

[54] GUIDING DEVICE FOR TREATMENT ACCESSORIES OF AN ENDOSCOPE

[75] Inventor: Teruo Ouchi, Tokyo, Japan

[73] Assignee: Asahi Kogaku Kogyo Kabushiki Kaisha, Tokyo, Japan

[21] Appl. No.: 826,513

[22] Filed: Apr. 3, 1997

[30] Foreign Application Priority Data

May 13, 1996 [JP] Japan ..................................... 8-117192

[51] Int. Cl.⁶ ....................................................... A61B 1/04
[52] U.S. Cl. .......................... 600/123; 600/104; 600/106; 600/153
[58] Field of Search ..................................... 600/104, 123, 600/153, 154, 155, 156, 157, 158; 606/106, 205, 206

[56] References Cited

U.S. PATENT DOCUMENTS

| | | |
|---|---|---|
| 4,108,162 | 8/1978 | Chikashige et al. . |
| 4,178,810 | 12/1979 | Takahashi . |
| 4,245,624 | 1/1981 | Komiya ................................. 600/153 X |
| 4,271,845 | 6/1981 | Chikashige et al. . |
| 4,646,722 | 3/1987 | Silverstein et al. .................. 600/123 X |
| 4,741,326 | 5/1988 | Sidall et al. ............................. 600/123 |
| 5,050,585 | 9/1991 | Takahashi ............................... 600/123 |
| 5,386,818 | 2/1995 | Schneebaum et al. ............. 600/153 X |
| 5,702,344 | 12/1997 | Silverstein ........................... 600/123 X |

FOREIGN PATENT DOCUMENTS

| | | |
|---|---|---|
| 48-7832 | 2/1973 | Japan . |
| 53-107086 | 2/1977 | Japan . |
| 5253178 | 5/1993 | Japan . |

OTHER PUBLICATIONS

"Gastrointestinal Endoscopy", Matin B. Grossman, M.D., *Clinical Symposia*, vol. 32, No. 3, CIBA Pharmaceutical Company, Summit, New Jersey, 1980.

*Primary Examiner*—Beverly M. Flanagan
*Attorney, Agent, or Firm*—Greenblum & Bernstein, P.L.C.

[57] ABSTRACT

A guiding device for treatment accessories of an endoscope includes a guiding tube and a fixing device. The guiding tube is long enough to extend from a forceps channel of the endoscope and is provided with a bent portion at a distal end thereof. The fixing device positions the guiding tube to having a predetermined positional relationship with respect to the entrance of the forceps channel such that the bent portion bends in a predetermined direction with respect to the exit of the forceps channel.

10 Claims, 8 Drawing Sheets

GUIDING DEVICE FOR TREATMENT ACCESSORIES OF AN ENDOSCOPE

BACKGROUND OF THE INVENTION

The present invention relates to a guiding device for treatment accessories of an endoscope.

A treatment accessory of an endoscope is conventionally inserted through a forceps channel of the endoscope. When the endoscope is inserted into a human body, the distal end of the treatment accessory is extended from the forceps channel and is then guided to be accurately directed to an affected part.

A treatment accessory which is arranged such that the distal end thereof can be remotely controlled (i.e., controlled from a proximal end thereof) to bend is known. Examples of such a treatment accessory are disclosed in Japanese Utility Model Registration Publication No. SHO 48-7832, and Japanese Patent Provisional Pulication No. HEI 5-253178.

Figure 15:
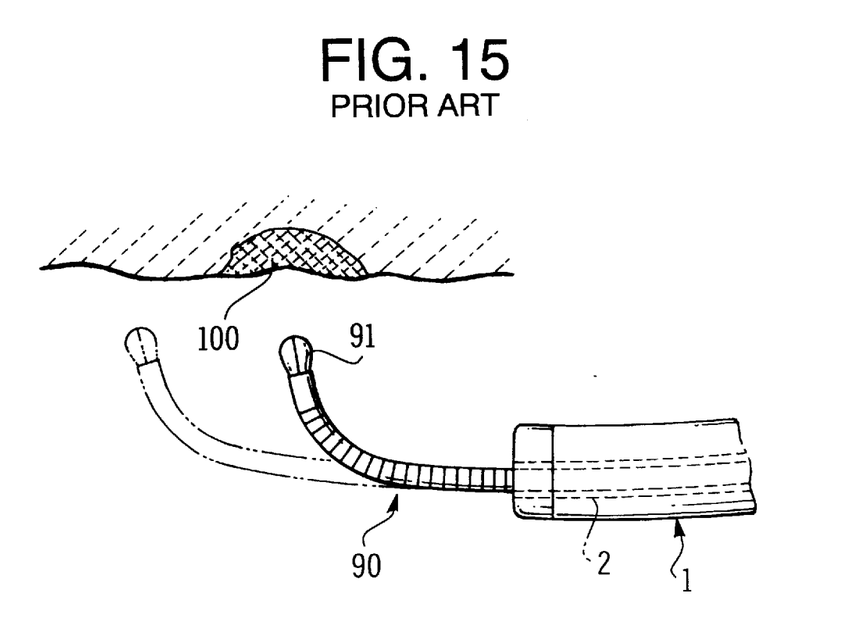
FIG. 15 illustrates the use of a conventional endoscope.

An example of a distal end 91 of such a treatment accessory 90 is shown in FIG. 15. In the treatment accessory 90, the distal end 91 can be remotely bent to be directed to the affected part 100. However, even though the distal end 91 may be bent remotely, it may be difficult to bring the treatment accessory 90 in contact with the affected part 100 since, even if the distal end 91 of the treatment accessory 90 is pushed out of a forceps channel 2 to try to bring the distal end 91 closer to the affected part 100, the distal end 91 moves in a direction parallel to the axis of the forceps channel 2 (shown by the dotted line), and the distal end 91 does not directly approach the affected part 100.

In order to deal with the above problem, the treatment accessory 90 described above may be inserted in a tube member and then the distal end of the tube member may also be remotely controlled (i.e., controlled from a proximal end thereof) to bend. (Described in Japanese Utility Model Registration Provisional Publication No. SHO 53-107086). In such a case, the distal end of the tube member is bent using a wire or the like. In particular, the distal end portion of the tube member is formed to have a certain elasticity such that the distal end portion bends when the wire is pulled, and straightens when the pulling force is released.

However, to use such a structure efficiently, operation of the endoscope, movement of the treatment accessory 90 (e.g., opening or closing of cup forceps), and movement of the distal end of the tube member must all be done simultaneously. In particular, the wire must be held in order to maintain a bend in the distal end portion of the tube member. This requires very complicated manipulation of operating elements, and accordingly it is difficult to use such a structure.

SUMMARY OF THE INVENTION

It is therefore an object of the invention to provide an improved guiding device with which a distal end of a treatment accessory of an endoscope can be accurately and easily directed to a desired position.

According to an aspect of the invention, there is provided a guiding device that includes a guiding tube that may be inserted through a forceps channel of an endoscope to guide a treatment accessory which is inserted in the guiding tube. In particular, the guiding tube has a distal end and a proximal end and the guiding tube is long enough that a distal portion of the guiding tube at the distal end thereof extends by a predetermined amount from an exit of the forceps channel. Further, the distal portion of the guiding tube is provided with a bent portion.

By providing the guiding tube with a bent portion, as the treatment accessory is pushed out of the guiding tube, the treatment accessory will be directed in an appropriate direction such that operation of the endoscope alone will allow a distal end of the treatment accessory to be brought into appropriate contact with an affected part.

In a preferred embodiment, the guiding device may further include a fixing device provided to the guiding tube at the proximal end. In this case, the fixing device may be detachably mounted to an entrance of the forceps channel such that the guiding tube may be oriented at any rotational direction with respect to an axis of the forceps channel at the entrance. Further, when the fixing device is mounted to the entrance, the distal portion of the guiding tube extends from the forceps channel by the predetermined amount.

In this way, the fixing device orients the guiding tube both rotationally and lengthwise and holds the guiding tube in a set position.

In another preferred embodiment, the guiding device may include a fixing device that is detachably mounted to an entrance of the forceps channel such that the guiding tube is inserted through the fixing device and is slidably and frictionally supported by the fixing device.

With the arrangement of this embodiment, the guiding tube is both adjustable rotationally and along the axis thereof such that the guiding tube may be made long enough to be used in various endoscopes having various lengths and inserted into the fixing device to an appropriate length.

In another preferred embodiment, the guiding tube is further provided with a directive bending portion. The directive bending portion is formed to have a tendency to bend easily in one direction. Further, the directive bending portion is formed such that, when the distal portion of the guiding tube is extended from the forceps channel, the directive bending portion corresponds to a bendable portion of the forceps channel. In particular, a direction in which the bent portion is bent and the direction in which the directive bending portion tends to bend have a predetermined relationship.

With the arrangement of this embodiment, when the bendable portion of the endoscope is bent, the guiding tube will automatically rotate such that the directive bending portion follows the bend of the bendable portion. Thus, due to the predetermined relationship between the directions of the bent portion and the directive bending portion, the bent portion can be directed by operation of the bendable portion of the endoscope.

In particular cases, the direction in which the bent portion is bent and the direction in which the directive bending portion tends to bend may be set accordingly, for example, to be the same direction.

Alternatively, rather than the directive bending portion, the guiding tube may be provided with a curved portion (i.e., a pre-curved portion) in order to produce a similar effect.

In the above embodiments, it may be preferable, for certain kinds of treatment, that the bent portion is bent through an angle greater than 90 degrees.

DESCRIPTION OF THE EMBODIMENTS

Figure 1:
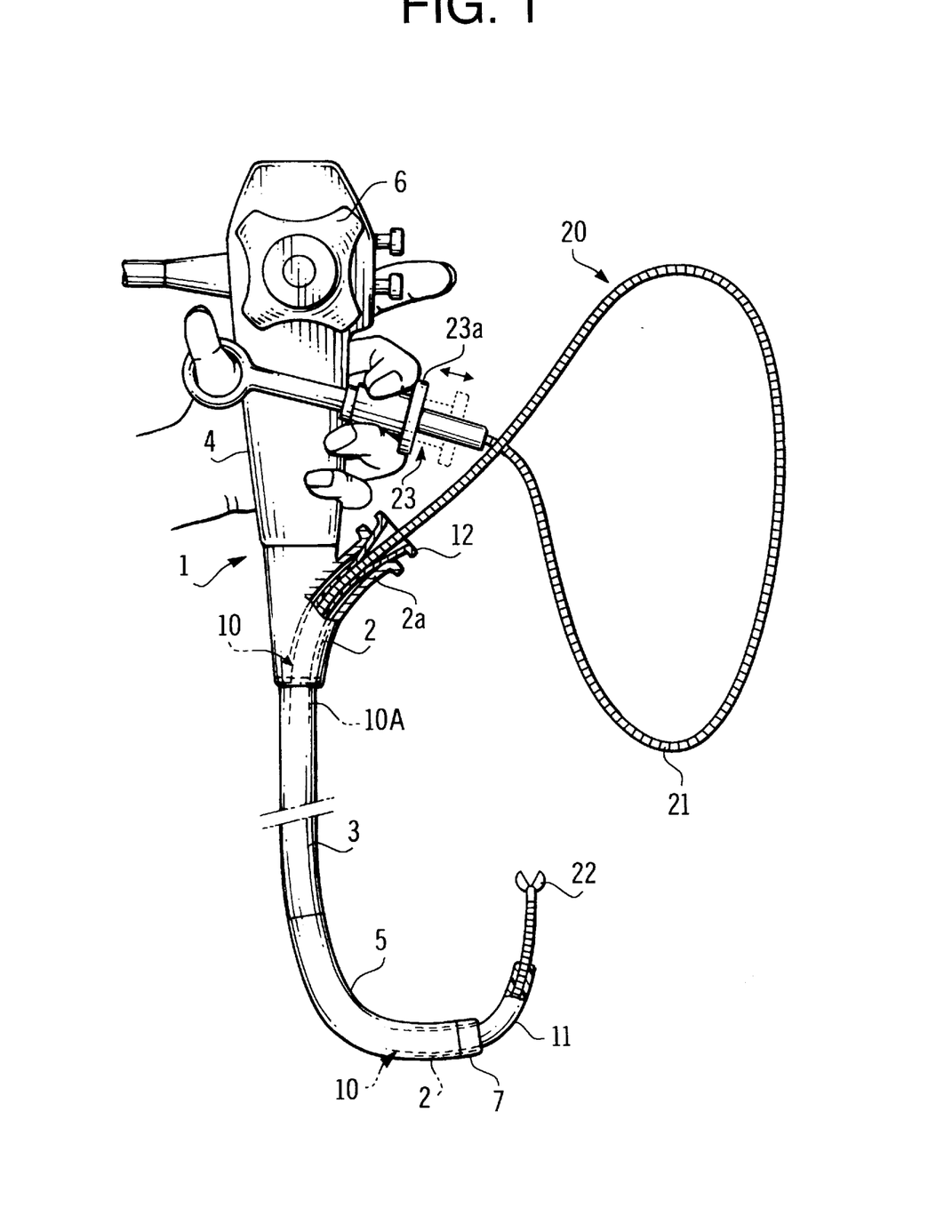
FIG. 1 is a schematic side view of an endoscope in which a guiding device according to an embodiment of the invention is inserted.

FIG. 1 is a schematic side view of an endoscope 1 in which a guiding device 10 according to an embodiment of the invention is inserted. In particular, the guiding device 10 is inserted in a forceps channel 2 of the endoscope 1. Further, a treatment accessory 20 is inserted in the guiding device 10. In this embodiment, as a particular example, the treatment accessory 20 is a biopsy forceps instrument.

The endoscope 1 includes a flexible insertion tube 3 to be inserted in a human cavity, a manipulating unit 4 connected at the proximal end of the insertion tube 3, and a bendable tube 5 provided at the distal end of the insertion tube 3. The bendable tube 5 is bent in a desired direction by operating a knob 6 provided on the manipulating unit 4. An end section 7 that accommodates an objective lens and the like for observing inside the human cavity is provided at the distal end of the bendable tube 5.

The guiding device 10 is made from a relatively hard but flexible synthetic resin, for example, polyimide resin, nylon, tetrafluoroethylen or the like. The guiding device 10 includes a guiding tube 10A, a bent portion 11 provided at a distal end of the guiding tube 10A, and a mixing mouth piece 12 provided at a proximal end of the guiding tube 10A. The guiding tube 10A and the bent portion 11 may be inserted into or removed from the forceps channel 2 of the endoscope 1.

The bent portion 11 may, for example, be formed integrally with the guiding tube 10A or may be connected thereto. In particular, the bent portion 11 is arc-shaped having a predetermined radius of curvature such that the bent portion 11 is bent at a predetermined angle. Since the bent portion 11 and the guiding tube 10A are made of a synthetic resin, the guiding tube 10A can be curved or bent and the bent portion 11 can be straightened if an external force is applied. Further, the guiding tube 10A and the bent portion 11 return to an original shape (straight or bent, respectively) when the external force is released.

The fixing mouth piece 12 may be formed integrally with the guiding tube 10A or may be connected to the guiding tube 10A. The fixing mouth piece 12 is formed to be firmly fitted in a receiving mouth piece 2a that is provided on the manipulating unit 4. In particular, the cross sections, along a plane perpendicular to an insertion direction of the guiding tube 10A, of both the fixing mouth piece 12 and the receiving mouth piece 2a are preferably circular such that the fixing mouth piece 12 fits in the receiving mouth piece 2a regardless of the orientation of the fixing mouth piece 12 about the axis of the receiving mouth piece 2a. The fixing mouth piece 12 fits into the receiving mouth piece 2a such that the fixing mouth piece 12 may be rotated with respect to the receiving mouth piece 2a by an application of a predetermined force.

The length of the guiding tube 10A is slightly greater than the length of the forceps channel 2 such that, when the guiding tube 10A is fully inserted inside the forceps channel 2 and the fixing mouth piece 12 is firmly fitted in the receiving mouth piece 2a, the distal end of the guiding tube 10A, including the bent portion 11, extends from an outlet of the forceps channel 2 formed at the end section 7.

The guiding device 10 is inserted in the forceps channel 2 through the receiving mouth piece 2a (i.e., from the manipulation unit 4). In order to insert the guiding device 10, the bent portion 11 is first deformed to follow the shape of the forceps channel 2 during insertion. Next, the guiding tube 10A is inserted until the bent portion 11 extends from the distal end of the forceps channel 2 (i.e., from the end section 7). When the bent portion 11 extends from the end of the forceps channel 2, the bent portion 11 returns to its original bent shape.

In this state, depending on the orientation of the fixing mouth piece 12 with respect to the axis of the receiving mouth piece 2a, the orientation of the curved section 11 with respect to the axis of the end section 7 will vary. Further, since the bent portion 11 is within a field of view of the endoscope 1, the orientation of the bent portion 11 (i.e., the direction in which the bent portion 11 is bent in relation to the axis of the end section 7) can be adjusted accurately by applying a force to rotate the fixing mouth piece 12 while observing the bent portion 11 through the endoscope 1.

Next, a treatment accessory 20,; such as biopsy forceps instrument,; is inserted in the guiding device 10 through the fixing mouth piece 12. The treatment accessory 20 (i.e., the biopsy forceps instrument as an example) includes a flexible sheath 21 (for example, a closely wound coil pipe) and a pair of cup forceps 22 provided at the end of the sheath 21. The cup forceps 22 may be opened and closed by an opening/closing mechanism (not shown), for example, a wire member which is slidably inserted through the sheath 21. The proximal end of the wire member is connected to an operating portion 23 that includes a slider 23a such that, by operating the slider 23a, an operator may remotely open or close the cup forceps 22.

The treatment accessory 20 is inserted in the guiding device 10 through the fixing mouth piece 12 with the cup forceps 22 closed, and the treatment accessory 20 is pushed until, as shown in FIG. 1, the cup forceps 22 extends from the distal end of the guiding device 10.

In this condition, since the fixing mouth piece 12 is fixedly fitted in the receiving mouth piece 2a, the distal end of the treatment accessory 20 is directed in a direction determined by the orientation of the bent portion 11.

At this stage, as shown in FIG. 1, the operator of the endoscope 1 operates both the manipulation unit 4 and the operating portion 23 with, for example, a left hand. Further, the operator may then pull or push the sheath 21 of the treatment accessory 20 with a right hand (not shown). Thus, a procedure can be performed by the operator alone. If the operating portion 23 is manipulated by an assistant, the operator's role becomes easier.

The bendable portion 5 of the endoscope 1 can also be utilized to direct the bent portion 11 in a desired direction. When the bendable portion 5 is utilized to direct the bent portion 11, it is preferable that the fixing mouth piece 12 be only loosely engaged with the receiving mouth piece 2a so that the guiding tube 10A rotates inside the forceps channel 2.

Figure 2:
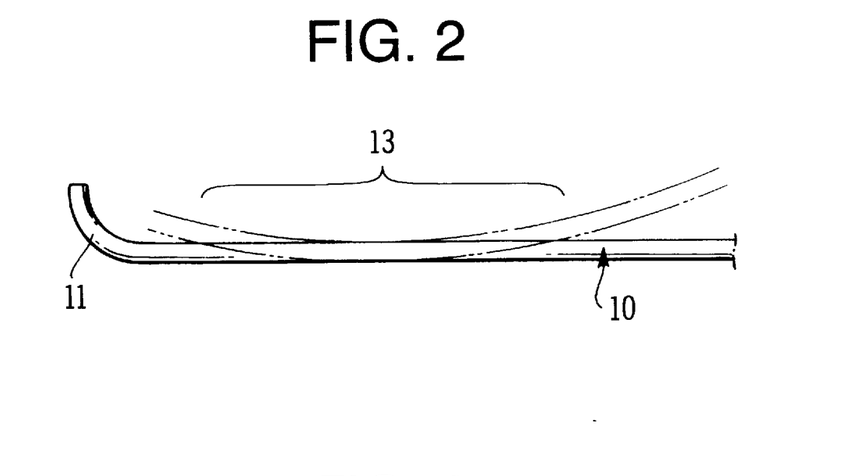
FIG. 2 is a side view of a distal end of the guiding device.

In particular, as shown in FIG. 2, it is preferable that a portion of the guiding tube 10A be provided with a directive bendable portion 13 that is located at the bendable portion 5 of the endoscope 1 when the bent portion 11 extends from the distal end of the forceps channel 2.

Figure 3:
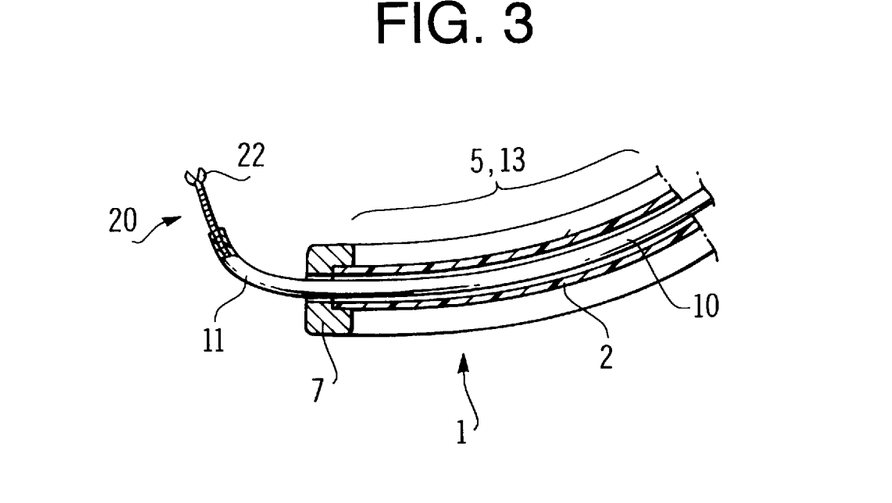
FIG. 3 is a side sectional view of a distal end of the endoscope showing the guiding device of FIG. 2.

The directive bendable portion 13 is formed such that the directive bendable portion 13 is neutrally straight but has a tendency to bend in a predetermined direction when an external force is applied, as shown by the phantom lines in FIG. 2. In FIG. 2, the predetermined direction is similar to the direction of curvature of the bent portion 11. As shown in FIG. 3, when the bendable tube 5 of the endoscope 1 is bent, the guiding device 10 tends to rotate such that the curving direction of the directive bendable portion 13 coincides with the bending direction of the bendable portion 5 of the endoscope 1.

In this case, since the bent portion 11 of the guiding device 10 is directed in the same direction as the direction in which the bendable portion 5 is bent, the bent portion 11 can be directed to a desired position by bending the bendable portion 5 of the endoscope 1.

Figure 4:
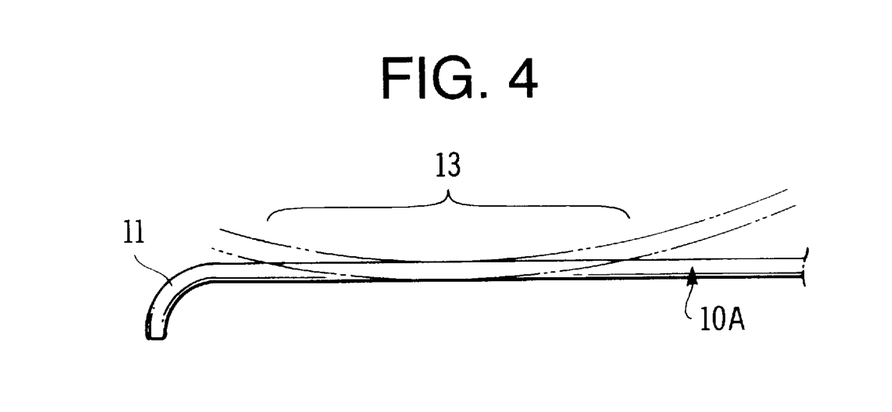
FIG. 4 is a side view of an alternate configuration of the distal end of the guiding device.
Figure 5:
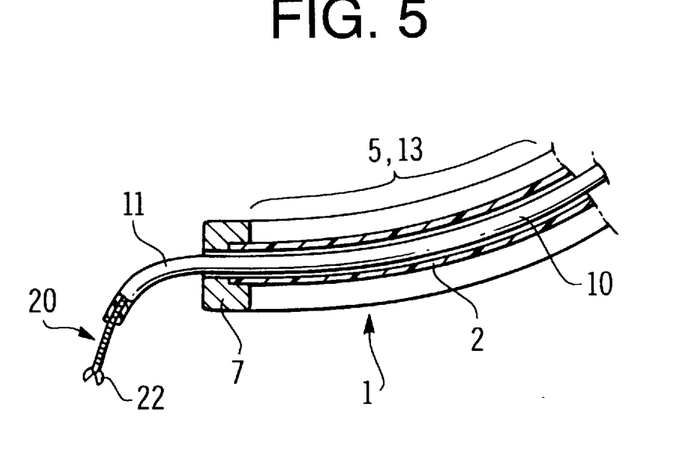
FIG. 5 is a side sectional view of a distal end of the endoscope showing the guiding device of FIG. 4.

Alternatively, the directive bendable portion 13 may be formed to tend to bend in another direction, for example, a direction opposite to the bend in the bent portion 11, as shown in FIG. 4. In this case, the bent portion 11 will be directed in an opposite direction to the curvature of the bendable portion 5 when the bendable portion 5 is bent, as shown in FIG. 5.

Note that, as described briefly above, the directive bendable portion 13 is not bent in advance, but is neutrally straight. The directive bendable portion 13 may be formed, for example, by forming a side wall of the guiding tube 10A (i.e., a predetermined arc of the circumference of the guiding tube 10A) to be thinner than the other side wall such that the directive bendable portion 13 will always bend toward the thinner side wall inside the bendable portion 5 when the bendable portion 5 is bent and the guiding tube 10A is free to rotate.

Figure 6:
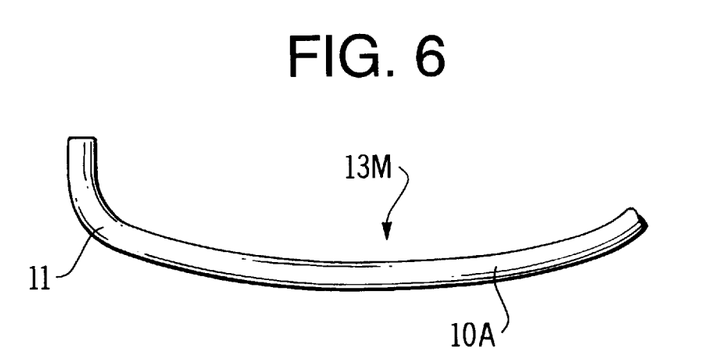
FIG. 6 is a side view of another alternate configuration of the distal end of the guiding device.
Figure 7:
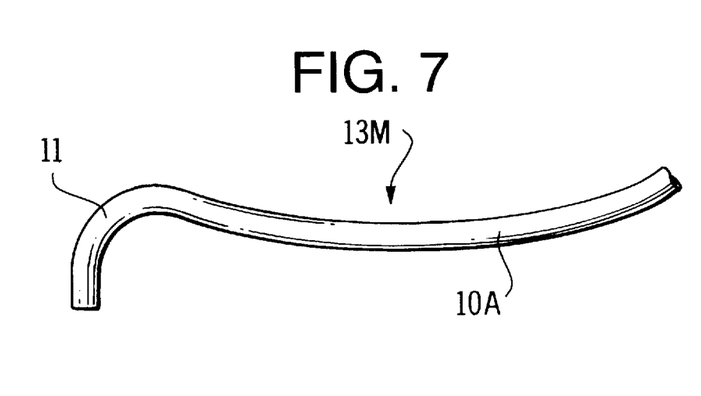
FIG. 7 is a side view of yet another alternate configuration of the distal end of the guiding device.

Alternatively, as shown in FIGS. 6 and 7, the guiding tube 10A may be formed to have a curved portion 13M (i.e., having a curved neutral state) instead of the directive bendable portion 13. FIG. 6 shows the guiding tube 10A in which the curved portion 13M is curved in the same direction as the bend in the bent portion 11 (similar to FIG. 2). FIG. 7 shows the guiding tube 10A in which the curved portion 13M is curved in an opposite direction to the bend in the bent portion 11 (similar to FIG. 4). As above, when the bendable portion 5 of the endoscope 1 is bent, the guiding tube 10A rotates such that the curved portion 13M follows the bend of the bendable portion 5 and similar effects as described above are obtained.

Figure 8:
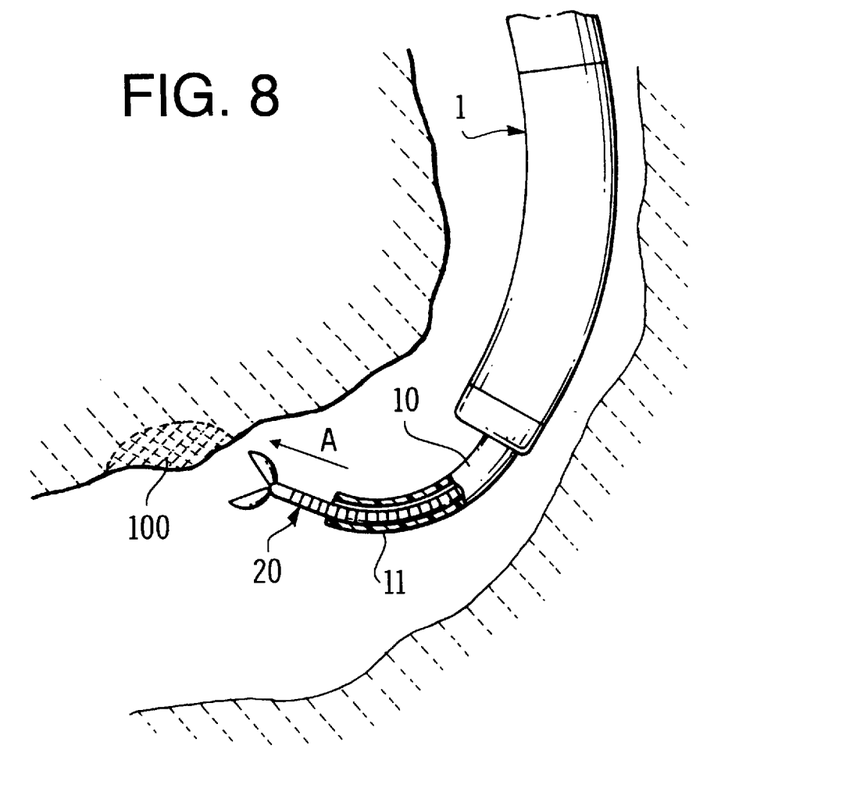
FIG. 8 illustrates the use of the endoscope shown in FIG. 1.

FIG. 8 shows a situation in which the above-described guiding device 10 is used. When the end portion of the guiding device 10 is directed to an affected part 100, and the treatment accessory 20 is pushed, the distal end of the treatment accessory 20 is directly brought into contact with the affected part 100 (i.e., moves in the direction of the arrow A). Thus, the affected part 100 can be treated accurately and easily.

Figure 9:
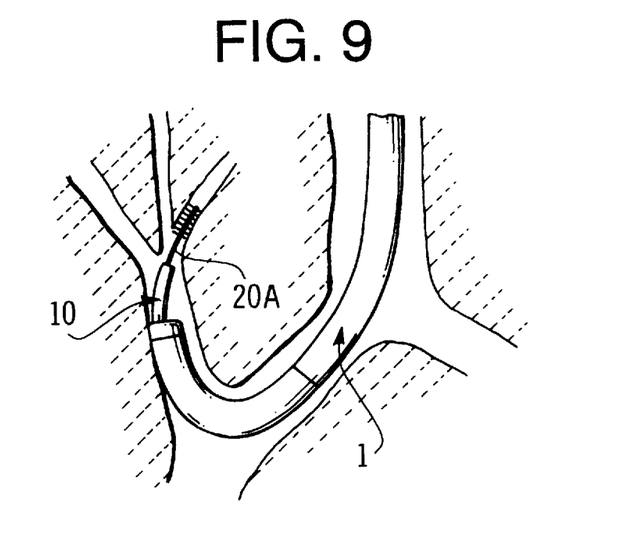
FIG. 9 illustrates the use of the endoscope shown in FIG. 1 in a bronchial tube.

FIG. 9 shows a situation where the guiding device 10 is used in the endoscope 1 in a bronchial tube. With use of the guiding device 10, a treatment accessory 20A such as a biopsy brush instrument or the like may be inserted into an upper right branch of the bronchial tubes.

Figure 10:
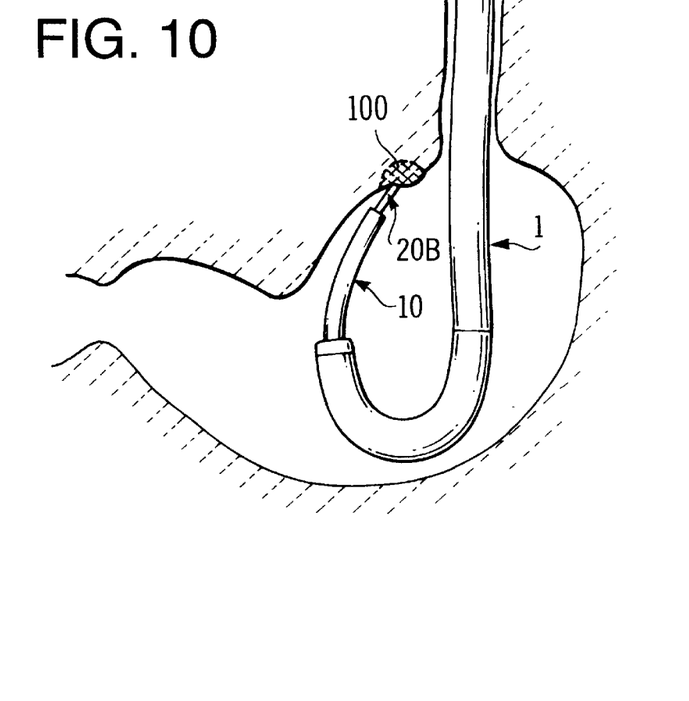
FIG. 10 illustrates the use of the endoscope shown in FIG. 1 in a stomach.

FIG. 10 shows a situation where the guiding device 10 is used in the endoscope 1 in a stomach. In FIG. 10, the affected part 100 is located at a point on an upper curvature of the stomach at which it is impossible to perform an injection by only bending of the endoscope 1. In this case, the use of the guiding device 10 allows the needle of the injector instrument to be inserted substantially normal to the surface of the affected part 100.

Figure 11:
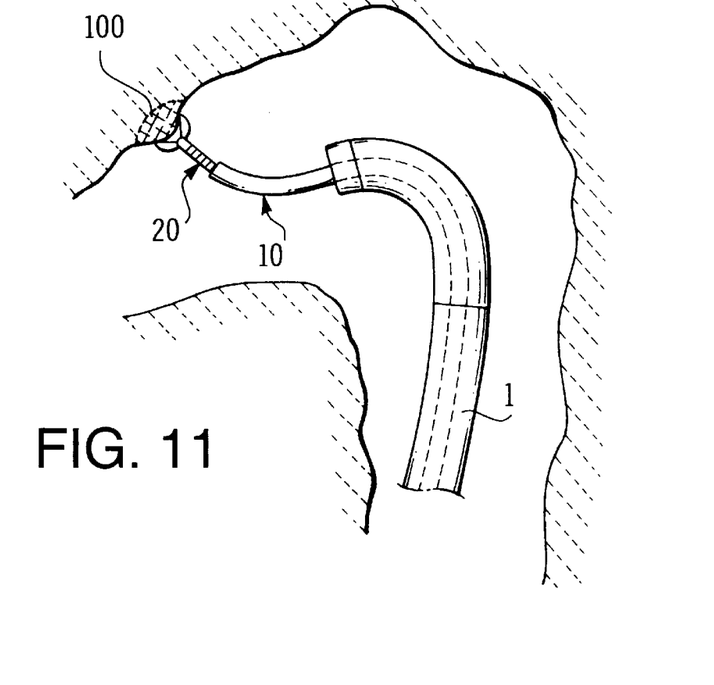
FIG. 11 illustrates the use of the endoscope shown in FIG. 1 in a large intestine.

FIG. 11 shows a situation where the guiding device 10 is used in the endoscope 1 in a large intestine. An this case, even inside a bent cavity, where treatment is usually difficult, the affected part 100 can be directly treated from an appropriate angle.

Figure 12:
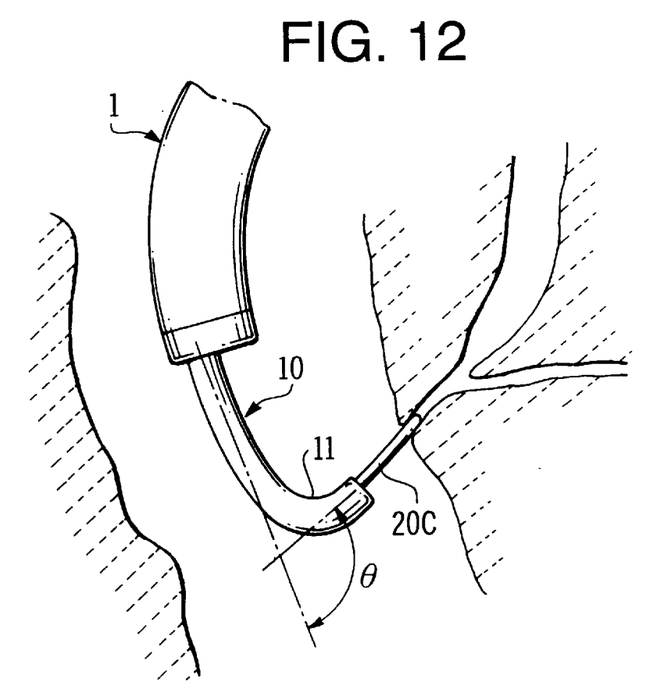
FIG. 12 illustrates the use of the endoscope shown in FIG. 1 in a duodenum.

FIG. 12 shows a situation where the guiding device 10 is used in the endoscope 1 in a duodenum. In this case, a treatment accessory 20C, for example an imaging tube instrument, can be inserted in a bile duct or pancreatic duct. Generally, insertion of the treatment accessory 20C in such a duct is considered to be impossible using a forward-viewing type endoscope 1, and, as such, a side-viewing type endoscope has had to be used. However, according to the embodiment, if the angle θ of the bent portion 11 is set at more than 90 degrees (e.g., 90–120 degrees), as shown in FIG. 12, the treatment can be performed with the forward-viewing type endoscope 1.

Figure 13:
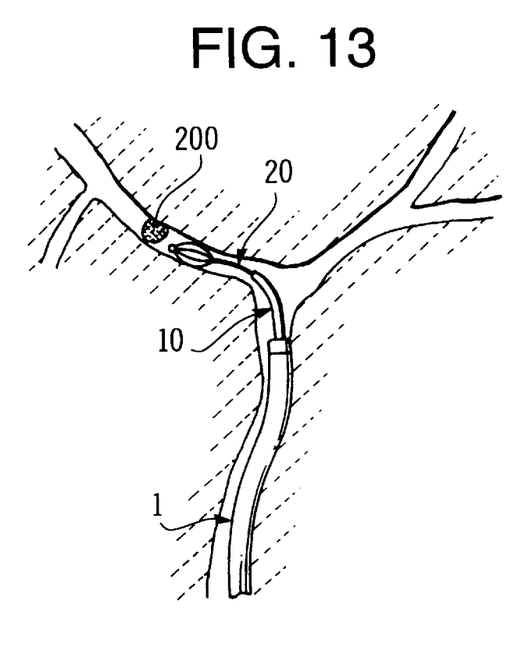
FIG. 13 illustrates the use of the endoscope shown in FIG. 1 to collect an intrahepatic stone.

FIG. 13 shows a situation in which an intrahepatic stone 200 is collected using the treatment accessory 20. In this case, the treatment accessory 20 may be a basket-shaped collector or the like, and the guide device 10 is inserted in a baby-scope (a very thin endoscope) 1.

Figure 14:
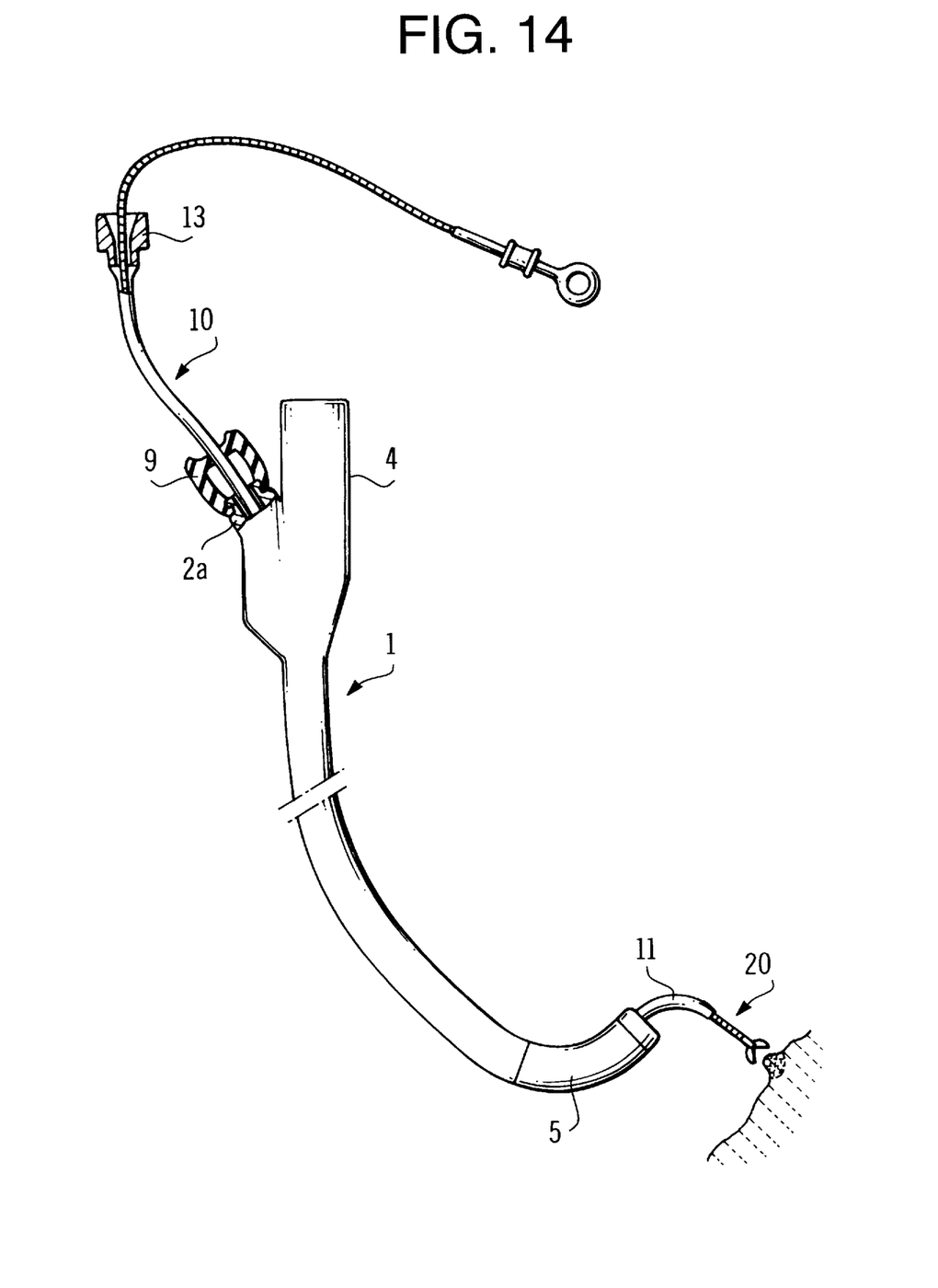
FIG. 14 is a schematic side view of an endoscope in which a guiding device according to another embodiment of the invention is inserted.

FIG. 14 shows another embodiment of the guiding device 10. In this embodiment, a frictional engagement piece 9 is coupled to the receiving mouth piece 2a for frictionally engaging a desired portion of the guiding device 10.

In the case shown in FIG. 14, the guiding device 10 is formed to be longer than the embodiment shown in FIG. 1, and further, rather than the fixing mouth piece 12 of the first embodiment, an insertion mouth piece 13 is provided at the proximal end of the guiding device 10. The treatment accessory 20 is inserted through the insertion mouth piece 13.

The frictional engaging piece 9 is, for example, made of rubber having a slit at the center thereof. In this case, when the guiding device 10 is inserted through the slit of the frictional engaging piece 9, the guiding device 10 is supported and is prevented from moving either along the axis of the receiving mouth piece 2a or rotatingly by a frictional force applied by the frictional engaging piece 9. Thus, the frictional engaging piece 9 supports the bent portion 11 to be directed in a desired direction.

According to the invention, by providing the arc-shaped bent portion 11 at the distal end of the guiding device 10 that is inserted in the forceps channel 2 of the endoscope 1, the tip of the treatment accessory 20 can be moved in a desired direction by controlling the rotational position of the guiding device 10. Further, the rotational position of the guiding device 10 can be controlled by bending the bendable portion 5 of the endoscope 1.

Insertion of the guiding device 10 through the forceps channel 2 of the endoscope 1 is now described.

Firstly, the endoscope 1 (i.e., the forceps channel 2) is straightened, then, the guiding device 10 is inserted along the straightened forceps channel 2. Initially, since the bent portion 11 is flexible, the bent portion 11 may be straightened when inserted in the forceps channel 2, and accordingly the guiding device 10 can be inserted smoothly.

Figure 16:
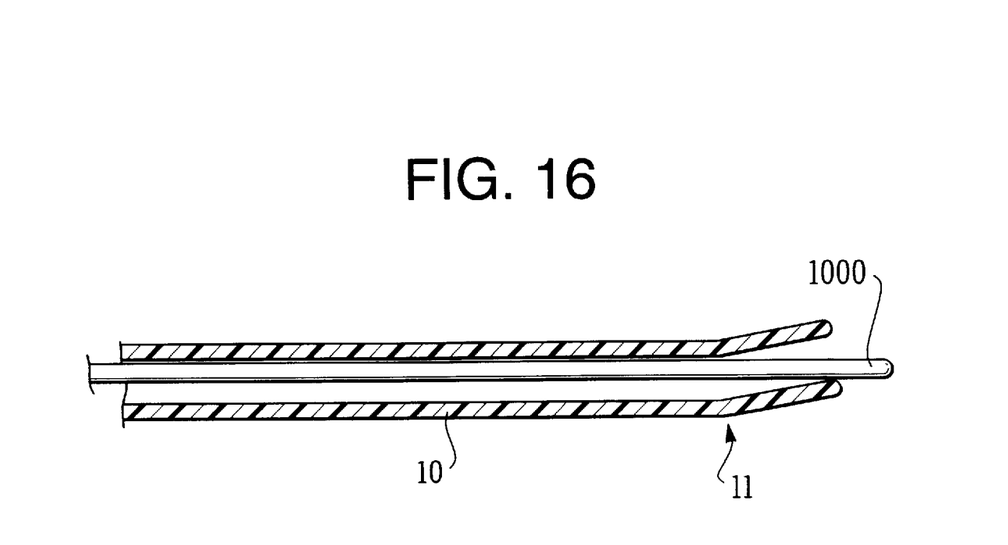
FIG. 16 illustrates the use of a mandrel member during insertion of the guiding device in the endoscope.

Alternatively, as shown in FIG. 16, a mandrel member 1000 or the like can be used in order to insert the guiding device 10 through the forceps channel smoothly and easily. The mandrel member 1000 is substantially straight and may be made from, for example, a stainless steel single or twisted wire having a certain elasticity. Firstly, the mandrel member 1000 is inserted through the guiding device 10 and the bent portion 11 is straightened by the mandrel member 1000. The guiding device 10, with the mandrel member 1000 inserted therein, is then inserted in the forceps channel 2 of the endoscope 1. As shown in FIG. 16, even if the forceps channel 2 is slightly bent, the guiding device 10 can be inserted through the forceps channel 2. When the distal end of the guiding device 10 extends from the end of the forceps channel 2, the mandrel member 1000 is removed. The guiding device 10 then returns its original shape (i.e., the bent portion 11 bends). After the mandrel member 1000 is removed, the treatment accessory 20 is inserted in the guiding device 10.

The present disclosure relates to subject matter contained in Japanese Patent Application No. HEI 8-117192, filed on May 13, 1996, which is expressly incorporated herein by reference in its entirety.

What is claimed is:

1. A guiding device in combination with an endoscope, comprising a guiding tube inserted through a forceps channel of said endoscope to guide a treatment accessory which is inserted in said guiding tube, said guiding tube having a distal end and a proximal end, a distal portion of said guiding tube at said distal end extending by a predetermined amount from an exit of said forceps channel, said distal portion of said guiding tube being provided with a bent portion, said guiding tube being further provided with a directive bending portion, said guiding tube being formed to have a tendency to bend easily in one direction, said directive bending portion corresponding to, when said distal portion of said guiding tube is extended from said forceps channel, a bendable portion of said forceps channel, such that a direction in which said bent portion is bent and said direction in which said directive bending portion tends to bend have a predetermined relationship.

2. The guiding device in combination with an enclosure according to claim 1, further comprising a fixing device being provided to said guiding tube at said proximal end, said fixing device detachably mounted to an entrance of said forceps channel such that said guiding tube may be oriented at any rotational direction with respect to an axis of said forceps channel at said entrance, wherein said distal portion of said guiding tube extends from said forceps channel by said predetermined amount when said fixing device is mounted to said entrance.

3. The guiding device in combination with an enclosure according to claim 1, further comprising a fixing device detachably mounted to an entrance of said forceps channel such that said guiding tube is inserted through said fixing device and is slidably and frictionally supported by said fixing device.

4. The guiding device in combination with an enclosure according to claim 1, wherein said direction in which said bent portion is bent and said direction in which said directive bending portion tends to bend are the same direction.

5. The guiding device in combination with an enclosure according to claim 1, wherein said direction in which said bent portion is bent and said direction in which said directive bending portion tends to bend are opposite directions.

6. A guiding device in combination with an endoscope, comprising a guiding tube inserted through a forceps channel of said endoscope to guide a treatment accessory which is inserted in said guiding tube, said guiding tube having a distal end and a proximal end, a distal portion of said guiding tube at said distal end extending by a predetermined amount from an exit of said forceps channel, said distal portion of said guiding tube being provided with a bent portion, wherein said guiding tube is further provided with a curved portion, said curved portion being formed to curve in one direction, said curved portion corresponding to, when said distal portion of said guiding tube is extended from said forceps channel, a bendable portion of said forceps channel, such that a direction in which said bent portion is bent and said direction in which said curved portion curves have a predetermined relationship.

7. The guiding device in combination with an enclosure according to claim 6, wherein said direction in which said bent portion is bent and said direction in which said curved portion curves are the same direction.

8. The guiding device in combination with an enclosure according to claim 6, wherein said direction in which said bent portion is bent and said direction in which said curved portion curves are opposite directions.

9. The guiding device in combination with an endoscope according to claim 6 further comprising a fixing device provided to said guiding tube at said proximal end, said fixing device being detachably mounted to an entrance of said forceps channel such that said guiding tube may be oriented at any rotational direction with respect to an axis of said forceps channel at said entrance, wherein said distal portion of said guiding tube extends from said forceps channel by said predetermined amount when said fixing device is mounted to said entrance.

10. The guiding device in combination with an endoscope according to claim 6, further comprising a fixing device mounted to an entrance of said forceps channel such that said guiding tube is inserted through said fixing device and is slidably and frictionally supported by said fixing device.

* * * * *

UNITED STATES PATENT AND TRADEMARK OFFICE
CERTIFICATE OF CORRECTION

PATENT NO. : 5,820,546        Page 1 of 2
DATED : October 13, 1998
INVENTOR(S) : Teruo Ouchi It is certified that error appears in the above-identified patent and that said Letters Patent is hereby corrected as shown below:

At column 7, line 53, (claim 2, line 1) of the printed patent, "enclosure" should be ---endoscope---.

At column 7, line 55 (claim 2, line 3) of the printed patent, delete "being".

At column 7, line 56 (claim 2, line 4) of the printed patent, after "device" insert ---being---.

At column 8, line 5, (claim 3, line 1) of the printed patent, "enclosure" should be ---endoscope---.

At column 8, line 11, (claim 4, line 1) of the printed patent, "enclosure" should be ---endoscope---.

At column 8, line 15, (claim 5, line 1) of the printed patent, "enclosure" should be ---endoscope---.

At column 8, line 35, (claim 7, line 1) of the printed patent, "enclosure" should be ---endoscope---.

UNITED STATES PATENT AND TRADEMARK OFFICE
CERTIFICATE OF CORRECTION

PATENT NO. : 5,820,546
DATED : October 13, 1998
INVENTOR(S) : Teruo OUCHI

It is certified that error appears in the above-identified patent and that said Letters Patent is hereby corrected as shown below:

At column 8, line 39, (claim 8, line 1) of the printed patent, "enclosure" should be —endoscope—.

Signed and Sealed this

Fourth Day of January, 2000

Attest:

*Attesting Officer*    *Acting Commissioner of Patents and Trademarks*